United States Patent
Boudreaux

(10) Patent No.: US 9,566,062 B2
(45) Date of Patent: Feb. 14, 2017

(54) SURGICAL INSTRUMENT WITH SECONDARY JAW CLOSURE FEATURE

(71) Applicant: Ethicon Endo-Surgery, Inc., Cincinnati, OH (US)

(72) Inventor: Chad P. Boudreaux, Cincinnati, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 857 days.

(21) Appl. No.: 13/692,211

(22) Filed: Dec. 3, 2012

(65) Prior Publication Data

US 2014/0151428 A1    Jun. 5, 2014

(51) Int. Cl.
| | |
|---|---|
| *A61B 18/00* | (2006.01) |
| *A61B 17/068* | (2006.01) |
| *A61B 18/14* | (2006.01) |
| *A61B 17/29* | (2006.01) |

(52) U.S. Cl.
CPC ......... *A61B 17/068* (2013.01); *A61B 18/1445* (2013.01); *A61B 18/1447* (2013.01); *A61B 2017/2933* (2013.01); *A61B 2017/2936* (2013.01); *A61B 2018/1455* (2013.01)

(58) Field of Classification Search
CPC ............. A61B 2018/00601; A61B 2018/0063; A61B 2018/1452; A61B 2018/1457; A61B 18/08; A61B 18/082; A61B 18/1442; A61B 18/1445; A61B 17/29; A61B 17/295; A61B 2017/2913; A61B 2017/2926; A61B 2017/2932; A61B 2017/2933; A61B 2017/2939

See application file for complete search history.

(56) References Cited

U.S. PATENT DOCUMENTS

| | | | |
|---|---|---|---|
| 5,509,922 A | 4/1996 | Aranyi et al. | |
| 6,500,176 B1 | 12/2002 | Truckai et al. | |
| 6,905,497 B2 | 6/2005 | Truckai et al. | |
| 7,101,371 B2 * | 9/2006 | Dycus ............... | A61B 18/1445 606/205 |
| 7,112,201 B2 | 9/2006 | Truckai et al. | |
| 7,125,409 B2 | 10/2006 | Truckai et al. | |

(Continued)

OTHER PUBLICATIONS

International Search Report dated Jun. 17, 2014 for Application No. PCT/US2013/072640.

(Continued)

*Primary Examiner* — Joseph Stoklosa
*Assistant Examiner* — Nicole L Pobre
(74) *Attorney, Agent, or Firm* — Frost Brown Todd LLC

(57) ABSTRACT

An apparatus for operating on tissue includes an outer sheath, upper and lower jaws connected at a pivot point, and a firing beam comprising a distal pair of flanges. The firing beam is configured to be received within slots defined in the upper and lower jaws to close the jaws. A proximal portion of the upper jaw defines a lever arm, and a free end of the lever arm extends proximally past a distal end of the lower jaw and proximally past the pivot point. The lever arm includes a pair of segments defining a portion of the slot of the upper jaw. The segments are configured for receipt through an outer sheath aperture. The pair of segments are operable to abut a distal end of the distal pair of flanges or be driven by the distal pair of flanges to assist with closure of the jaws.

20 Claims, 16 Drawing Sheets

(56) References Cited

U.S. PATENT DOCUMENTS

| | | | |
|---|---|---|---|
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,309,849 B2 | 12/2007 | Truckai et al. | |
| 7,311,709 B2 | 12/2007 | Truckai et al. | |
| 7,354,440 B2 | 4/2008 | Truckal et al. | |
| 7,381,209 B2 | 6/2008 | Truckai et al. | |
| 2009/0209946 A1* | 8/2009 | Swayze | A61B 17/3401 606/1 |
| 2011/0087218 A1 | 4/2011 | Boudreaux et al. | |
| 2011/0251612 A1* | 10/2011 | Faller | A61B 18/1445 606/52 |
| 2012/0078243 A1 | 3/2012 | Worrell et al. | |
| 2012/0078244 A1 | 3/2012 | Worrell et al. | |
| 2012/0078247 A1 | 3/2012 | Worrell et al. | |
| 2012/0078248 A1 | 3/2012 | Worrell et al. | |
| 2012/0083783 A1 | 4/2012 | Davison et al. | |
| 2012/0116379 A1 | 5/2012 | Yates et al. | |
| 2013/0023868 A1 | 1/2013 | Worrell et al. | |
| 2013/0030428 A1 | 1/2013 | Worrell et al. | |

OTHER PUBLICATIONS

International Search Report and Written Opinion dated Jun. 17, 2014 re Application No. PCT/US2013/072640.

International Preliminary Report on Patentability dated Jun. 9, 2015 re Application No. PCT/US2013/072640.

\* cited by examiner

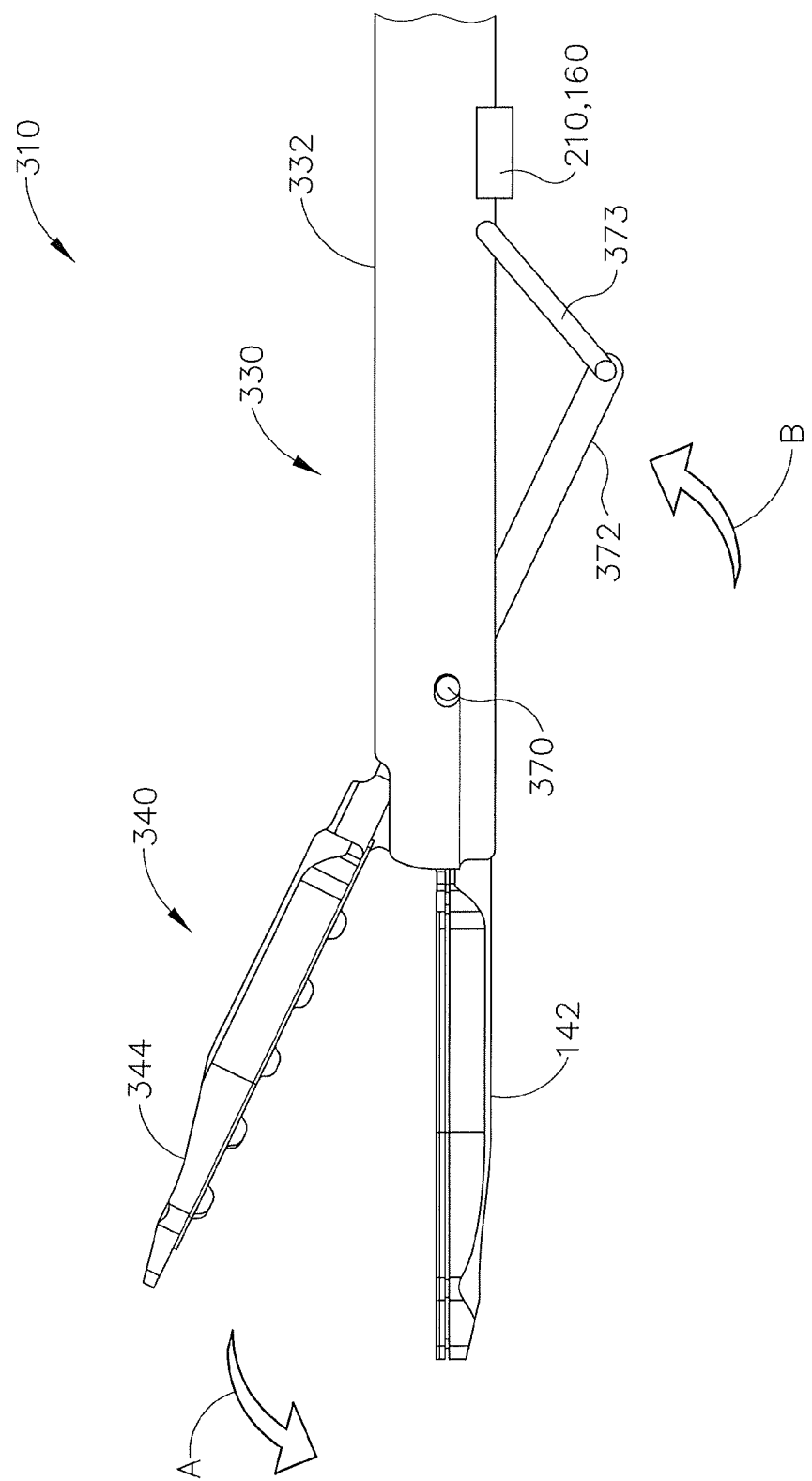

SURGICAL INSTRUMENT WITH SECONDARY JAW CLOSURE FEATURE

BACKGROUND

A variety of surgical instruments include a tissue cutting element and one or more elements that transmit radio frequency ("RF") energy to tissue (e.g., to coagulate or seal the tissue). An example of such a device is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, now U.S. Pat. No. 8,938,974, issued Jan. 27, 2015, the disclosure of which is incorporated by reference herein; U.S. Pub. No. 2012/0116379, entitled "Motor Driven Electrosurgical Device with Mechanical and Electrical Feedback," published May 10, 2012, now U.S. Pat. No. 9,161,803, issued Oct. 20, 2015, the disclosure of which is incorporated by reference herein; U.S. Pub. No. 2012/0078243, entitled "Control Features for Articulating Surgical Device," published Mar. 29, 2012, the disclosure of which is incorporated by reference herein; U.S. Pub. No. 2012/0078247, entitled "Articulation Joint Features for Articulating Surgical Device," published Mar. 29, 2012, now U.S. Pat. No. 9,402,682, issued Aug. 2, 2016, the disclosure of which is incorporated by reference herein; U.S. patent application Ser. No. 13/622,729, entitled "Surgical Instrument with Multi-Phase Trigger Bias," filed Sep. 19, 2012, now U.S. Pat. No. 9,089,327, issued Jul. 28, 2015, the disclosure of which is incorporated by reference herein; and U.S. patent application Ser. No. 13/622,735, entitled "Surgical Instrument with Contained Dual Helix Actuator Assembly," filed Sep. 19, 2012, now U.S. Pub. No. 2013/0023868, published Jan. 24, 2013, the disclosure of which is incorporated by reference herein.

While several medical devices have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 11 depicts an exemplary alternative upper jaw of the end effector of FIG. 5 in which the upper arm includes a pair of linked lever arms.

Figure 1:
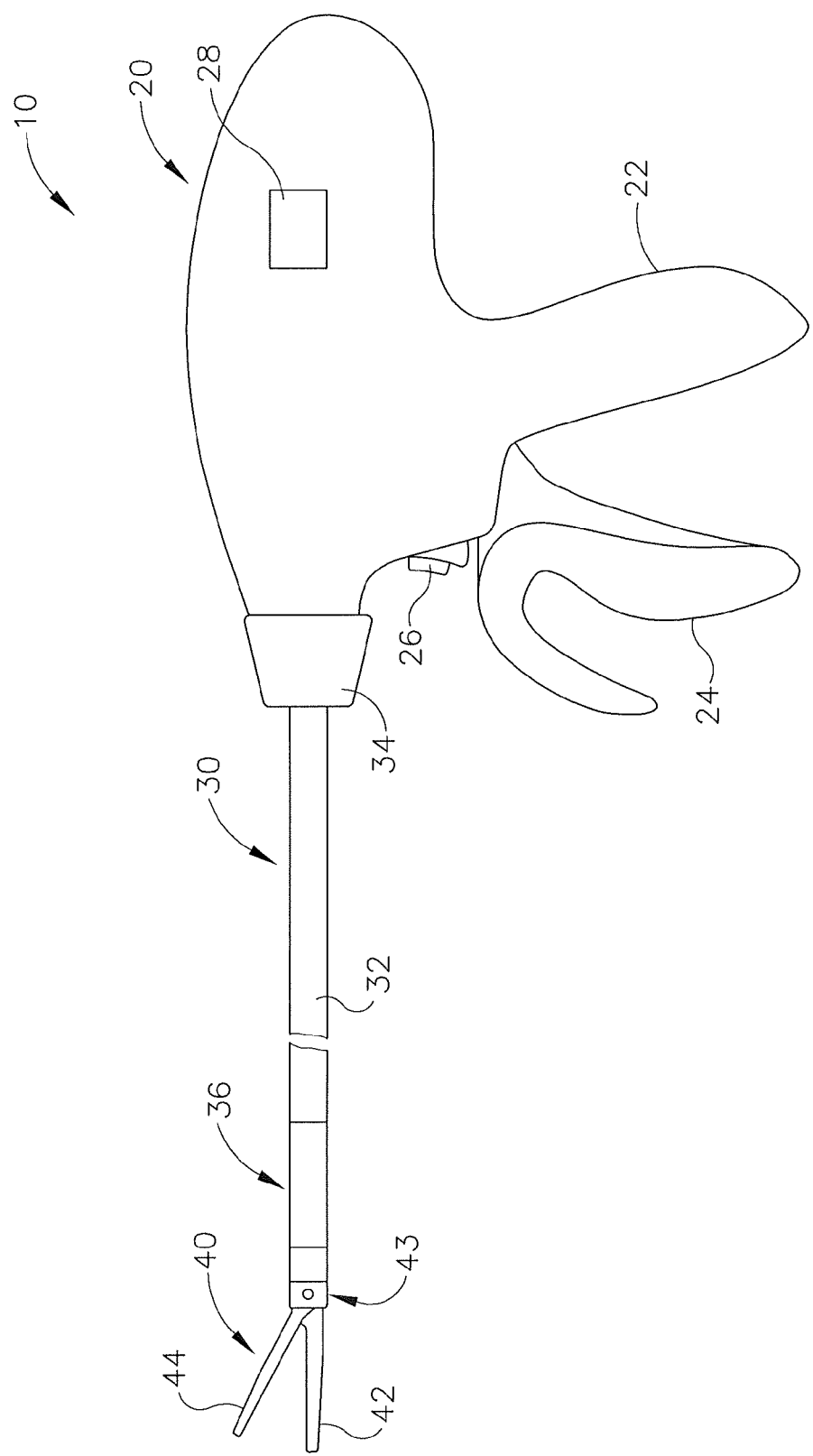
FIG. 1 depicts a side elevational view of an exemplary electrosurgical medical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Electrosurgical Device with Articulation Feature

FIGS. 1-4 show an exemplary electrosurgical instrument (10) that is constructed and operable in accordance with at least some of the teachings of U.S. Pat. No. 6,500,176; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pub. No. 2011/0087218, now U.S. Pat. No. 8,938,974, issued Jan. 27, 2015; U.S. Pub. No. 2012/0116379, now U.S. Pat. No. 9,161,803, issued Oct. 20, 2015; U.S. Pub. No. 2012/0078243; U.S. Pub. No. 2012/0078247, now U.S. Pat. No. 9,402,682, issued Aug. 2, 2016; U.S. patent application Ser. No. 13/622,729, now U.S. Pat. No. 9,089,372, issued Jul. 28, 2015; and/or U.S. patent application Ser. No. 13/622,735, now U.S. Pub. No. 2013/0023868, published Jan. 24, 2013. As described therein and as will be described in greater detail below, electrosurgical instrument (10) is operable to cut tissue and seal or weld tissue (e.g., a blood vessel, etc.) substantially simultaneously. In other words, electrosurgical instrument (10) operates similar to an endocutter type of stapler, except that electrosurgical instrument (10) provides tissue welding through application of bipolar RF energy instead of providing lines of staples to join tissue. It should also be understood that electrosurgical instrument (10) may have various structural and functional similarities with the ENSEAL® Tissue Sealing Device by Ethicon Endo-Surgery, Inc., of Cincinnati, Ohio. Furthermore, electrosurgical instrument (10) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to electrosurgical instrument (10), there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Exemplary Handpiece and Shaft

Electrosurgical instrument (10) of the present example includes a handpiece (20), a shaft (30) extending distally from handpiece (20), and an end effector (40) disposed at a distal end of shaft (30). Handpiece (20) of the present example includes a pistol grip (22), a pivoting trigger (24), an activation button (26), and an articulation control (28). Trigger (24) is pivotable toward and away from pistol grip (22) to selectively actuate end effector (40) as will be described in greater detail below. Activation button (26) is operable to selectively activate RF circuitry that is in communication with end effector (40), as will also be described in greater detail below. In some versions, activation button (26) also serves as a mechanical lockout against trigger (24), such that trigger (24) cannot be fully actuated unless button (26) is being pressed simultaneously. Examples of how such a lockout may be provided are disclosed in one or more of the references cited herein. In addition or in the alternative, trigger (24) may serve as an electrical and/or mechanical lockout against button (26), such that button (26) cannot be effectively activated unless trigger (24) is being squeezed simultaneously. It should be understood that pistol grip (22), trigger (24), and button (26) may be modified, substituted, supplemented, etc. in any suitable way, and that the descriptions of such components herein are merely illustrative.

Shaft (30) of the present example includes an outer sheath (32) and an articulation section (36). Articulation section (36) is operable to selectively position end effector (40) at various angles relative to the longitudinal axis defined by sheath (32). Articulation section (36) of shaft (30) may take a variety of forms. By way of example only, articulation section (36) may be configured in accordance with one or more teachings of U.S. Pub. No. 2012/0078247, now U.S. Pat. No. 9,402,682, issued Aug. 2, 2016, the disclosure of which is incorporated by reference herein. As another merely illustrative example, articulation section (36) may be configured in accordance with one or more teachings of U.S. Pub. No. 2012/0078248, entitled "Articulation Joint Features for Articulating Surgical Device," published Mar. 29, 2012, now U.S. Pat. No. 9,220,559, issued Dec. 29, 2015, the disclosure of which is incorporated by reference herein. Various other suitable forms that articulation section (36) may take will be apparent to those of ordinary skill in the art in view of the teachings herein. It should also be understood that some versions of instrument (10) may simply lack articulation section (36).

In some versions, shaft (30) is also rotatable about the longitudinal axis defined by sheath (32), relative to handpiece (20), via a knob (34). Such rotation may provide rotation of end effector (40) and shaft (30) unitarily. In some other versions, knob (34) is operable to rotate end effector (40) without rotating any portion of shaft (30) that is proximal of articulation section (36). As another merely illustrative example, electrosurgical instrument (10) may include one rotation control that provides rotatability of shaft (30) and end effector (40) as a single unit; and another rotation control that provides rotatability of end effector (40) without rotating any portion of shaft (30) that is proximal of articulation section (36). Other suitable rotation schemes will be apparent to those of ordinary skill in the art in view of the teachings herein. Of course, rotatable features may simply be omitted if desired.

Articulation control (28) of the present example is operable to selectively control articulation section (36) of shaft (30), to thereby selectively position end effector (40) at various angles relative to the longitudinal axis defined by shaft (30). By way of example only, some merely illustrative forms that articulation control (28) and other components of handpiece (20) may take are disclosed in U.S. Pub. No. 2012/0078243, the disclosure of which is incorporated by reference herein; in U.S. Pub. No. 2012/0078244, entitled "Control Features for Articulating Surgical Device," published Mar. 29, 2012, the disclosure of which is incorporated by reference herein; and in U.S. patent application Ser. No. 13/622,735, now U.S. Pub. No. 2013/0023868, published Jan. 24, 2013, the disclosure of which is incorporated by reference herein. Still other suitable forms that articulation control (28) may take will be apparent to those of ordinary skill in the art in view of the teachings herein. It should also be understood that some versions of instrument (10) may simply lack an articulation control (28).

B. Exemplary End Effector

End effector (40) of the present example comprises a first jaw (42) and a second jaw (44). In the present example, first jaw (42) is substantially fixed relative to shaft (30); while second jaw (44) pivots relative to shaft (30), toward and away from first jaw (42). In some versions, actuators such as rods or cables, etc., may extend through sheath (32) and be joined with second jaw (44) at a pivotal coupling (43), such that longitudinal movement of the actuator rods/cables/etc. through shaft (30) provides pivoting of second jaw (44) relative to shaft (30) and relative to first jaw (42). Of course, jaws (42, 44) may instead have any other suitable kind of movement and may be actuated in any other suitable fashion. By way of example only, and as will be described in greater detail below, jaws (42, 44) may be actuated and thus closed by longitudinal translation of a firing beam (60), such that actuator rods/cables/etc. may simply be eliminated in some versions.

Figure 2:
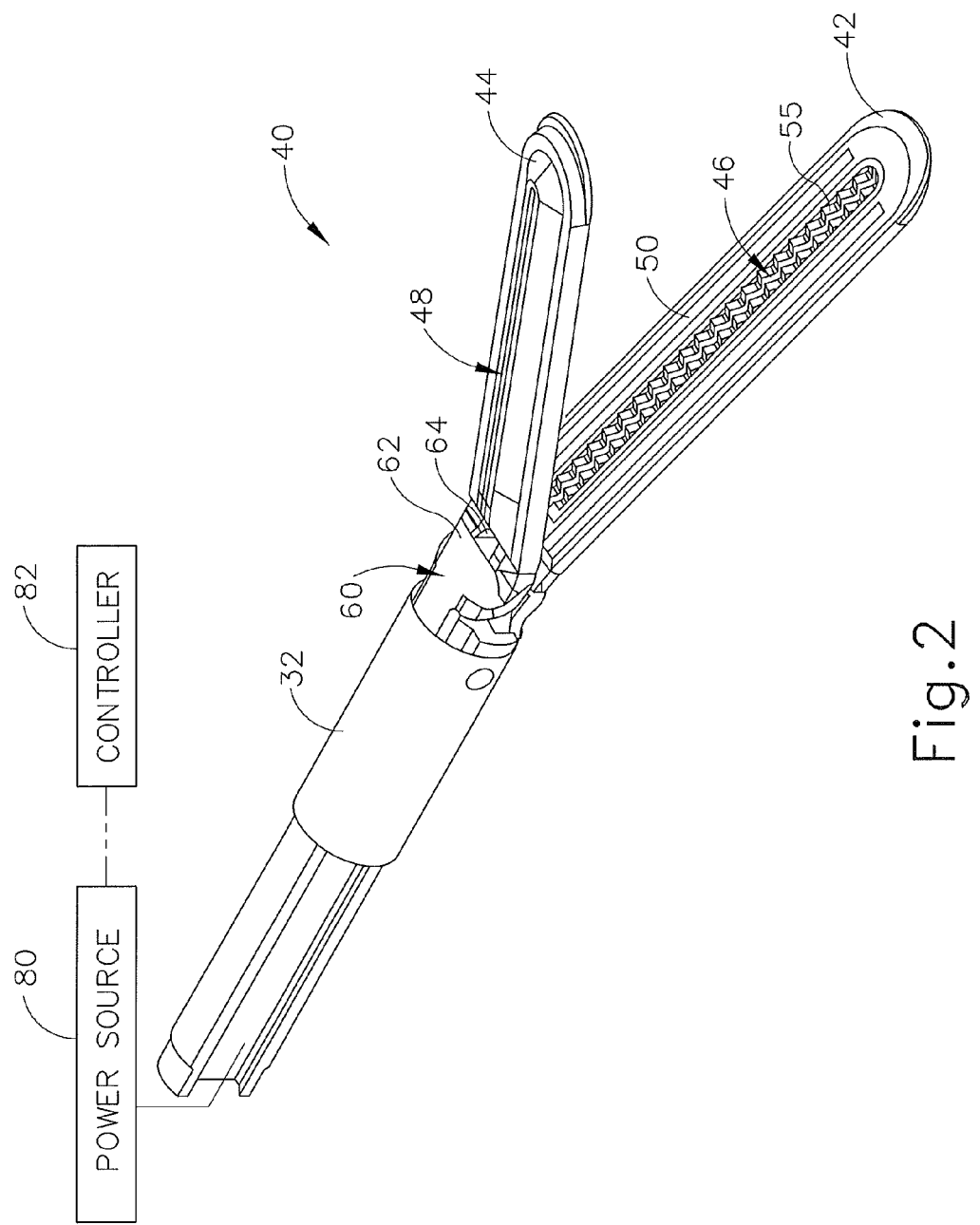
FIG. 2 depicts a perspective view of the end effector of the instrument of FIG. 1, in an open configuration.
Figure 3:
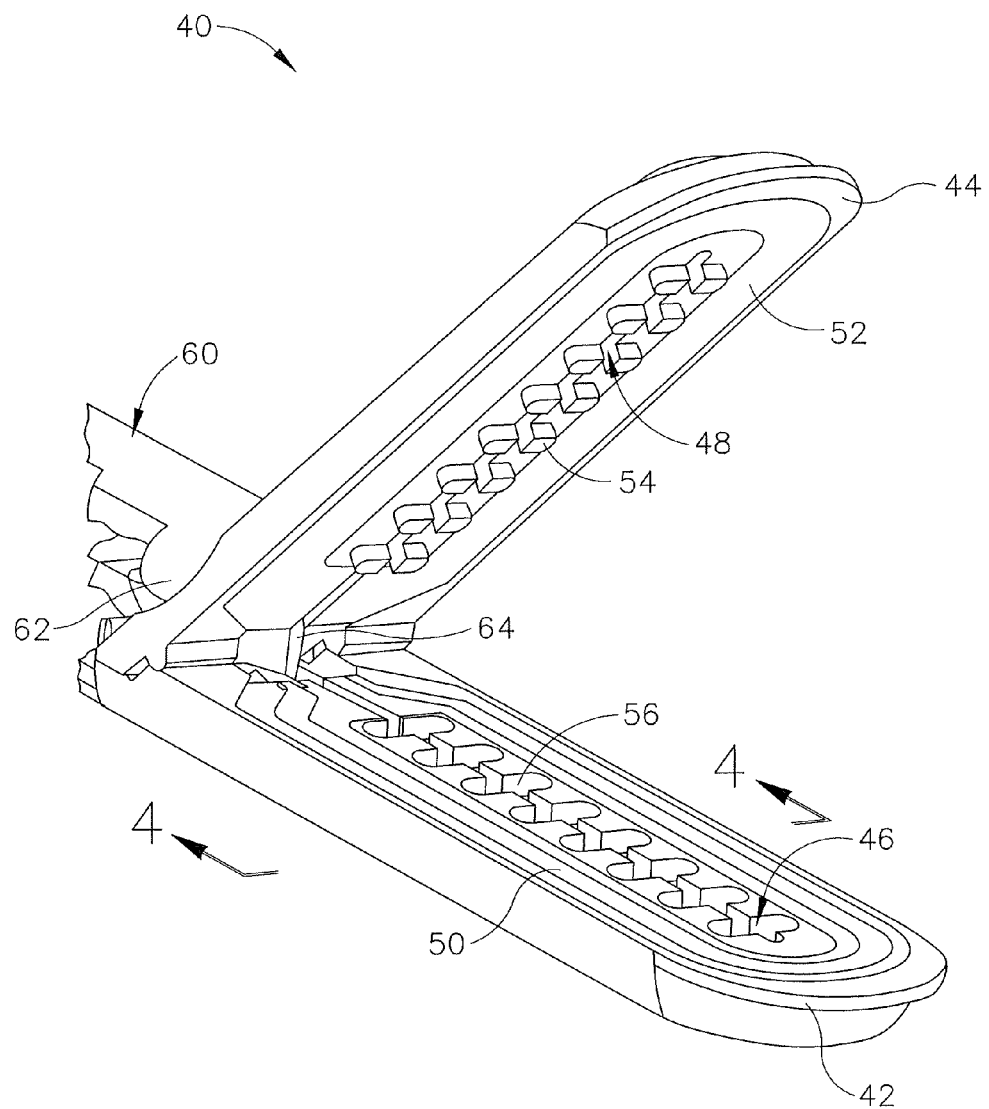
FIG. 3 depicts another perspective view of the end effector of the instrument of FIG. 1, in an open configuration.
Figure 4:
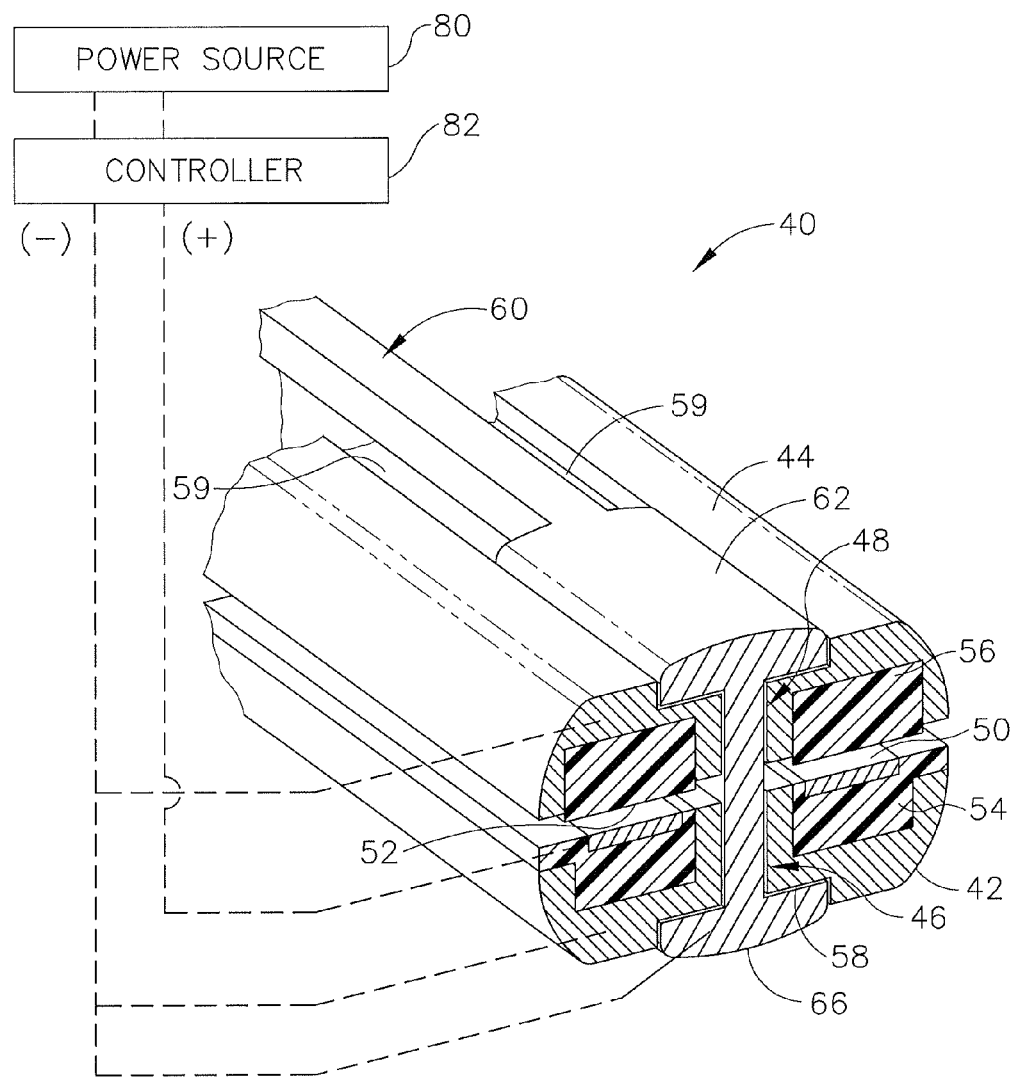
FIG. 4 depicts a cross-sectional end view of the end effector of FIG. 2, in a closed configuration and with the blade in a distal position.

As best seen in FIGS. 2-4, first jaw (42) defines a longitudinally extending elongate slot (46); while second jaw (44) also defines a longitudinally extending elongate slot (48). In addition, the top side of first jaw (42) presents a first electrode surface (50); while the underside of second jaw (44) presents a second electrode surface (52). Electrode surfaces (50, 52) are in communication with an electrical source (80) via one or more conductors (not shown) that extend along the length of shaft (30). Electrical source (80) is operable to deliver RF energy to first electrode surface (50) at a first polarity and to second electrode surface (52) at a second (opposite) polarity, such that RF current flows between electrode surfaces (50, 52) and thereby through tissue captured between jaws (42, 44). In some versions, firing beam (60) serves as an electrical conductor that cooperates with electrode surfaces (50, 52) (e.g., as a ground return) for delivery of bipolar RF energy captured between jaws (42, 44). Electrical source (80) may be external to electrosurgical instrument (10) or may be integral with electrosurgical instrument (10) (e.g., in handpiece (20), etc.), as described in one or more references cited herein or otherwise. A controller (82) regulates delivery of power from electrical source (80) to electrode surfaces (50, 52). Controller (82) may also be external to electrosurgical instrument (10) or may be integral with electrosurgical instrument (10) (e.g., in handpiece (20), etc.), as described in one or more references cited herein or otherwise. It should also be understood that electrode surfaces (50, 52) may be provided in a variety of alternative locations, configurations, and relationships.

As best seen in FIG. 4, the lower side of first jaw (42) includes a longitudinally extending recess (58) adjacent to slot (46); while the upper side of second jaw (44) includes a longitudinally extending recess (59) adjacent to slot (48). FIG. 2 shows the upper side of first jaw (42) including a plurality of teeth serrations (46). It should be understood that the lower side of second jaw (44) may include complementary serrations that nest with serrations (46), to enhance gripping of tissue captured between jaws (42, 44) without necessarily tearing the tissue. FIG. 3 shows an example of serrations (46) in first jaw (42) as mainly recesses; with serrations (48) in second jaw (44) as mainly protrusions. Of course, serrations (46, 48) may take any other suitable form or may be simply omitted altogether. It should also be understood that serrations (46, 48) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (42, 44).

With jaws (42, 44) in a closed position, shaft (30) and end effector (40) are sized and configured to fit through trocars having various inner diameters, such that electrosurgical instrument (10) is usable in minimally invasive surgery, though of course electrosurgical instrument (10) could also be used in open procedures if desired. By way of example only, with jaws (42, 44) in a closed position, shaft (30) and end effector (40) may present an outer diameter of approximately 5 mm. Alternatively, shaft (30) and end effector (40) may present any other suitable outer diameter (e.g., between approximately 2 mm and approximately 20 mm, etc.).

As another merely illustrative variation, either jaw (42, 44) or both of jaws (42, 44) may include at least one port, passageway, conduit, and/or other feature that is operable to draw steam, smoke, and/or other gases/vapors/etc. from the surgical site. Such a feature may be in communication with a source of suction, such as an external source or a source within handpiece (20), etc. In addition, end effector (40) may include one or more tissue cooling features (not shown) that reduce the degree or extent of thermal spread caused by end effector (40) on adjacent tissue when electrode surfaces (50, 52) are activated. Various suitable forms that such cooling features may take will be apparent to those of ordinary skill in the art in view of the teachings herein.

In some versions, end effector (40) includes one or more sensors (not shown) that are configured to sense a variety of parameters at end effector (40), including but not limited to temperature of adjacent tissue, electrical resistance or impedance of adjacent tissue, voltage across adjacent tissue, forces exerted on jaws (42, 44) by adjacent tissue, etc. By way of example only, end effector (40) may include one or more positive temperature coefficient (PTC) thermistor bodies (54, 56) (e.g., PTC polymer, etc.), located adjacent to electrodes (50, 52) and/or elsewhere. Data from sensors may be communicated to controller (82). Controller (82) may process such data in a variety of ways. By way of example only, controller (82) may modulate or otherwise change the RF energy being delivered to electrode surfaces (50, 52), based at least in part on data acquired from one or more sensors at end effector (40). In addition or in the alternative, controller (82) may alert the user to one or more conditions via an audio and/or visual feedback device (e.g., speaker, lights, display screen, etc.), based at least in part on data acquired from one or more sensors at end effector (40). It should also be understood that some kinds of sensors need not necessarily be in communication with controller (82), and may simply provide a purely localized effect at end effector (40). For instance, a PTC thermistor bodies (54, 56) at end effector (40) may automatically reduce the energy delivery at electrode surfaces (50, 52) as the temperature of the tissue and/or end effector (40) increases, thereby reducing the likelihood of overheating. In some such versions, a PTC thermistor element is in series with power source (80) and electrode surface (50, 52); and the PTC thermistor provides an increased impedance (reducing flow of current) in response to temperatures exceeding a threshold. Furthermore, it should be understood that electrode surfaces (50, 52) may be used as sensors (e.g., to sense tissue impedance, etc.). Various kinds of sensors that may be incorporated into electrosurgical instrument (10) will be apparent to those of ordinary skill in the art in view of the teachings herein. Similarly various things that can be done with data from sensors, by controller (82) or otherwise, will be apparent to those of ordinary skill in the art in view of the teachings herein. Other suitable variations for end effector (40) will also be apparent to those of ordinary skill in the art in view of the teachings herein.

C. Exemplary Firing Beam

As also seen in FIGS. 2-4, electrosurgical instrument (10) of the present example includes a firing beam (60) that is longitudinally movable along part of the length of end effector (40). Firing beam (60) is coaxially positioned within shaft (30), extends along the length of shaft (30), and translates longitudinally within shaft (30) (including articulation section (36) in the present example), though it should be understood that firing beam (60) and shaft (30) may have any other suitable relationship. Firing beam (60) includes a sharp distal blade (64), an upper flange (62), and a lower flange (66). As best seen in FIG. 3, distal blade (64) extends through slots (46, 48) of jaws (42, 44), with upper flange (62) being located above jaw (44) in recess (59) and lower flange (66) being located below jaw (42) in recess (58). The configuration of distal blade (64) and flanges (62, 66) provides an "I-beam" type of cross section at the distal end of firing beam (60). While flanges (62, 66) extend longitudinally only along a small portion of the length of firing beam (60) in the present example, it should be understood that flanges (62, 66) may extend longitudinally along any suitable length of firing beam (60). In addition, while flanges (62, 66) are positioned along the exterior of jaws (42, 44), flanges (62, 66) may alternatively be disposed in corresponding slots formed within jaws (42, 44). For instance, each jaw (42, 44) may define a "T"-shaped slot, with parts of distal blade (64) being disposed in one vertical portion of each "T"-shaped slot and with flanges (62, 66) being disposed in the horizontal portions of the "T"-shaped slots. Various other suitable configurations and relationships will be apparent to those of ordinary skill in the art in view of the teachings herein.

Distal blade (64) is substantially sharp, such that distal blade (64) will readily sever tissue that is captured between jaws (42, 44). Distal blade (64) is also electrically grounded in the present example, providing a return path for RF energy as described elsewhere herein. In some other versions, distal blade (64) serves as an active electrode. In addition or in the alternative, distal blade (64) may be selectively energized with ultrasonic energy (e.g., harmonic vibrations at approximately 55.5 kHz, etc.).

The "I-beam" type of configuration of firing beam (60) provides closure of jaws (42, 44) as firing beam (60) is advanced distally. In particular, flange (62) urges jaw (44) pivotally toward jaw (42) as firing beam (60) is advanced from a proximal position (FIGS. 1-3) to a distal position (FIG. 4), by bearing against recess (59) formed in jaw (44). This closing effect on jaws (42, 44) by firing beam (60) may occur before distal blade (64) reaches tissue captured between jaws (42, 44). Such staging of encounters by firing beam (60) may reduce the force required to squeeze grip (24) to actuate firing beam (60) through a full firing stroke. In other words, in some such versions, firing beam (60) may have already overcome an initial resistance required to substantially close jaws (42, 44) on tissue before encountering resistance from severing the tissue captured between jaws (42, 44). Of course, any other suitable staging may be provided.

In the present example, flange (62) is configured to cam against a ramp feature at the proximal end of jaw (44) to open jaw (44) when firing beam (60) is retracted to a proximal position and to hold jaw (44) open when firing beam (60) remains at the proximal position. This camming capability may facilitate use of end effector (40) to separate layers of tissue, to perform blunt dissections, etc., by forcing jaws (42, 44) apart from a closed position. In some other versions, jaws (42, 44) are resiliently biased to an open position by a spring or other type of resilient feature. While jaws (42, 44) close or open as firing beam (60) is translated in the present example, it should be understood that other versions may provide independent movement of jaws (42, 44) and firing beam (60). By way of example only, one or more cables, rods, beams, or other features may extend through shaft (30) to selectively actuate jaws (42, 44) independently of firing beam (60). Such jaw (42, 44) actuation features may be separately controlled by a dedicated feature of handpiece (20). Alternatively, such jaw actuation features may be controlled by trigger (24) in addition to having trigger (24) control firing beam (60). It should also be understood that firing beam (60) may be resiliently biased to a proximal position, such that firing beam (60) retracts proximally when a user relaxes their grip on trigger (24).

D. Exemplary Operation

In an exemplary use, end effector (40) is inserted into a patient via a trocar. Articulation section (36) is substantially straight when end effector (40) and part of shaft (30) are inserted through the trocar. Articulation control (28) may then be manipulated to pivot or flex articulation section (36) of shaft (30) in order to position end effector (40) at a desired position and orientation relative to an anatomical structure within the patient. Two layers of tissue of the anatomical structure are then captured between jaws (42, 44) by squeezing trigger (24) toward pistol grip (22). Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (10) is perpendicular to the longitudinal axis defined by end effector (40), etc.). In other words, the lengths of jaws (42, 44) may be oriented perpendicular to (or at least generally transverse to) the length of the blood vessel. As noted above, flanges (62, 66) cammingly act to pivot jaw (42) toward jaw (44) when firing beam (60) is actuated distally by squeezing trigger (24) toward pistol grip (22).

Jaws (42, 44) may be substantially clamping tissue before trigger (24) has swept through a full range of motion toward pistol grip (22), such that trigger (24) may continue pivoting toward pistol grip (22) through a subsequent range of motion after jaws (42, 44) have substantially clamped on the tissue.

With tissue layers captured between jaws (42, 44) firing beam (60) continues to advance distally by the user squeezing trigger (24) further toward pistol grip (22). As firing beam (60) continues to advance distally, distal blade (64) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (62, 66) immediately above and below jaws (42, 44), respectively, may help keep jaws (42, 44) in a closed and tightly clamping position. In particular, flanges (62, 66) may help maintain a significantly compressive force between jaws (42, 44). With severed tissue layer portions being compressed between jaws (42, 44), electrode surfaces (50, 52) are activated with bipolar RF energy by the user depressing activation button (26). In some versions, electrodes (50, 52) are selectively coupled with power source (80) (e.g., by the user depressing button (26), etc.) such that electrode surfaces (50, 52) of jaws (42, 44) are activated with a common first polarity while firing beam (60) is activated at a second polarity that is opposite to the first polarity. Thus, a bipolar RF current flows between firing beam (60) and electrode surfaces (50, 52) of jaws (42, 44), through the compressed regions of severed tissue layer portions. In some other versions, electrode surface (50) has one polarity while electrode surface (52) and firing beam (60) both have the other polarity. In either version (among at least some others), bipolar RF energy delivered by power source (80) ultimately thermally welds the tissue layer portions on one side of firing beam (60) together and the tissue layer portions on the other side of firing beam (60) together.

In certain circumstances, the heat generated by activated electrode surfaces (50, 52) can denature the collagen within the tissue layer portions and, in cooperation with clamping pressure provided by jaws (42, 44), the denatured collagen can form a seal within the tissue layer portions. Thus, the severed ends of the natural lumen defining anatomical structure are hemostatically sealed shut, such that the severed ends will not leak bodily fluids. In some versions, electrode surfaces (50, 52) may be activated with bipolar RF energy before firing beam (60) even begins to translate distally and thus before the tissue is even severed. For instance, such timing may be provided in versions where button (26) serves as a mechanical lockout relative to trigger (24) in addition to serving as a switch between power source (80) and electrode surfaces (50, 52). Other suitable ways in which instrument (10) may be operable and operated will be apparent to those of ordinary skill in the art in view of the teachings herein.

II. Exemplary End Effector Variations

Firing beam (60) closes jaws (42, 44) as described above by primarily driving upper jaw (44) at a location near a pivot positioned at a proximal end of jaws (42, 44). Driving upper jaw (44) near such a pivot may create a low mechanical advantage, and a minor gap at a proximal end of jaws (42, 44) may result in a multiplied gap spacing at a distal end of jaws (42, 44). A lever arm disposed at a proximal or rear end of upper jaw (44) and a camming interaction with such a lever arm may assist with increasing the mechanical advantage of the closure of jaws (42, 44), as described below.

Other features may also be provided to reduce the force required from a user (e.g., pivoting trigger (24) relative to pistol grip (22)) to drive firing beam (60) distally and/or to retract firing beam (60) proximally. In addition, features may be provided to effect forceful closure of jaws (42, 44) without firing beam (60) having to be driven distally to the point where firing beam (60) severs tissue. For example, a surgeon may wish to clamp and seal tissue before severing or cutting the tissue (or to clamp and seal tissue without cutting the tissue at all).

Additional exemplary modifications that may be provided for instrument (110, 310) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should also be understood that the below teachings are not limited to instrument (110, 310) or devices taught in the references cited herein. The below teachings may be readily applied to various other kinds of instruments, including instruments that would not be classified as radio frequency based endoscopic surgical instruments. Various other suitable devices and settings in which the below teachings may be applied will be apparent to those of ordinary skill in the art in view of the teachings herein.

A. Exemplary Upper Jaw with Lever Arm

Figure 5:
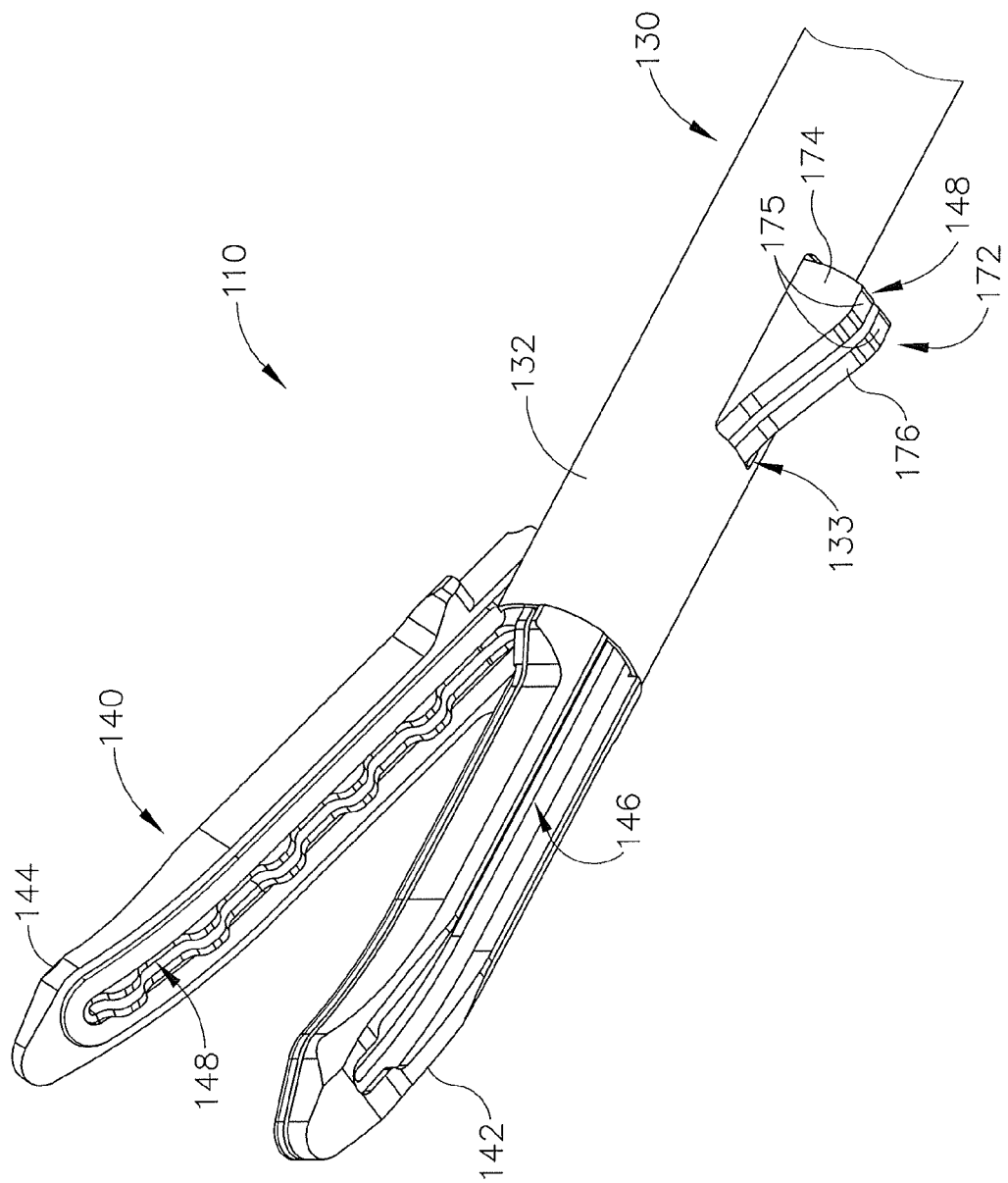
FIG. 5 depicts a perspective view of an exemplary end effector that may be incorporated into the instrument of FIG. 1, where the upper jaw has a lever arm.
Figure 6:
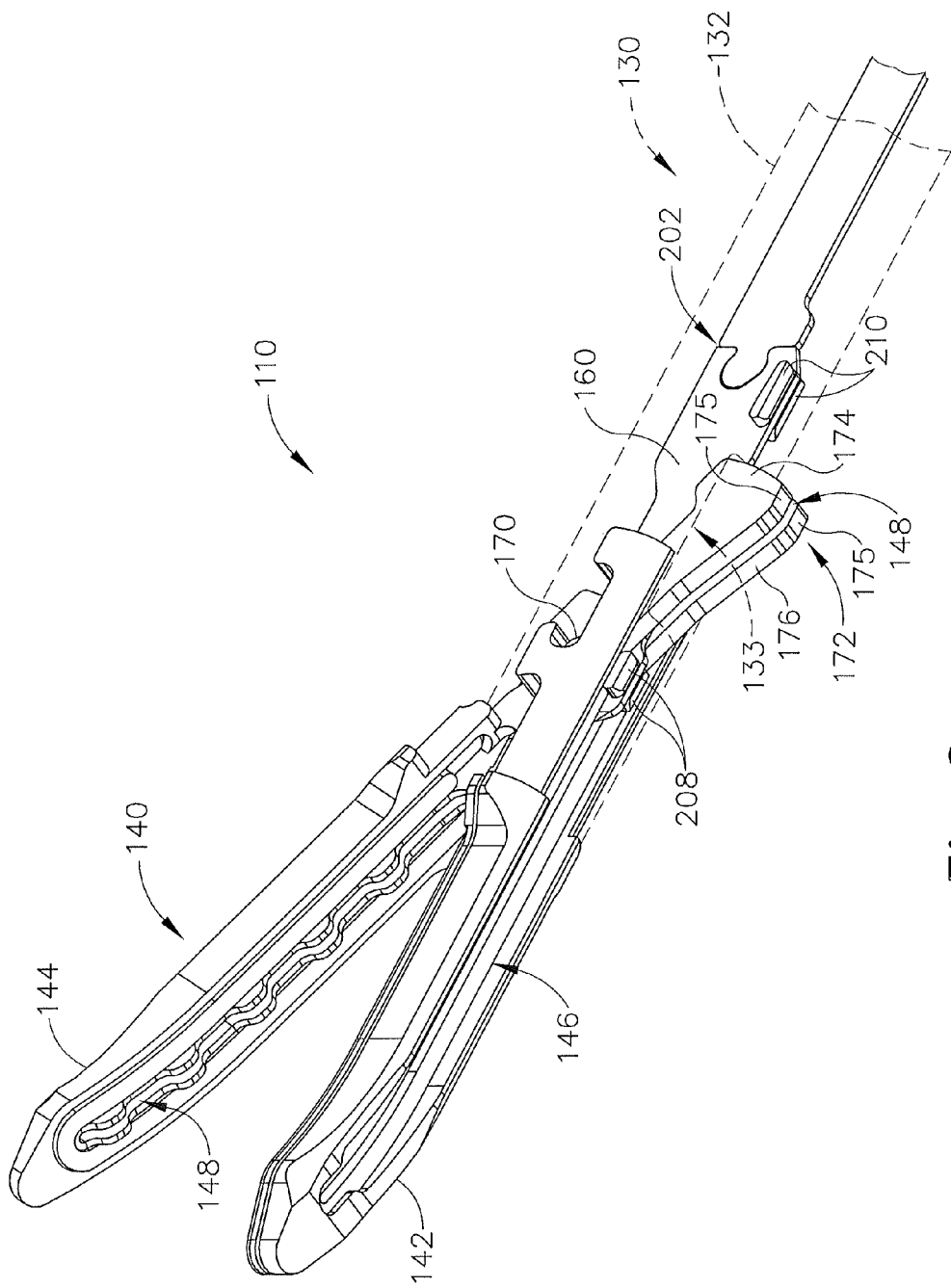
FIG. 6 depicts a perspective view of the end effector of FIG. 5 with the outer sheath shown in phantom lines and showing a firing beam having a pair of proximal flanges disposed within the outer sheath.

FIGS. 5-10F show an exemplary instrument (110) that is similar to instrument (10) described above except as described below. As shown in FIGS. 5-6, instrument (110) includes end effector (140) extending from outer sheath (132) of shaft (130). Instrument (310) is disposable within, for example, a 5 mm or less space defined by a trocar or other suitable tubular structure as will be apparent to those of skill in the art in view of the teachings herein. End effector (140) includes upper jaw (144) and lower jaw (142). A longitudinal axis of lower jaw (142) is substantially parallel to a longitudinal axis of outer sheath (132). Upper jaw (144) may be resiliently biased with respect to lower jaw (142) to an open position. Alternatively, retraction of firing beam (160), as described below, opens upper jaw (144) with respect to lower jaw (142). Firing beam (160) advances to close jaws (142, 144) in a manner similar to that described above with respect to firing beam (60) and jaws (42, 44) such that jaw (144) pivots about pivot pins (170) toward jaw (142).

Figure 7:
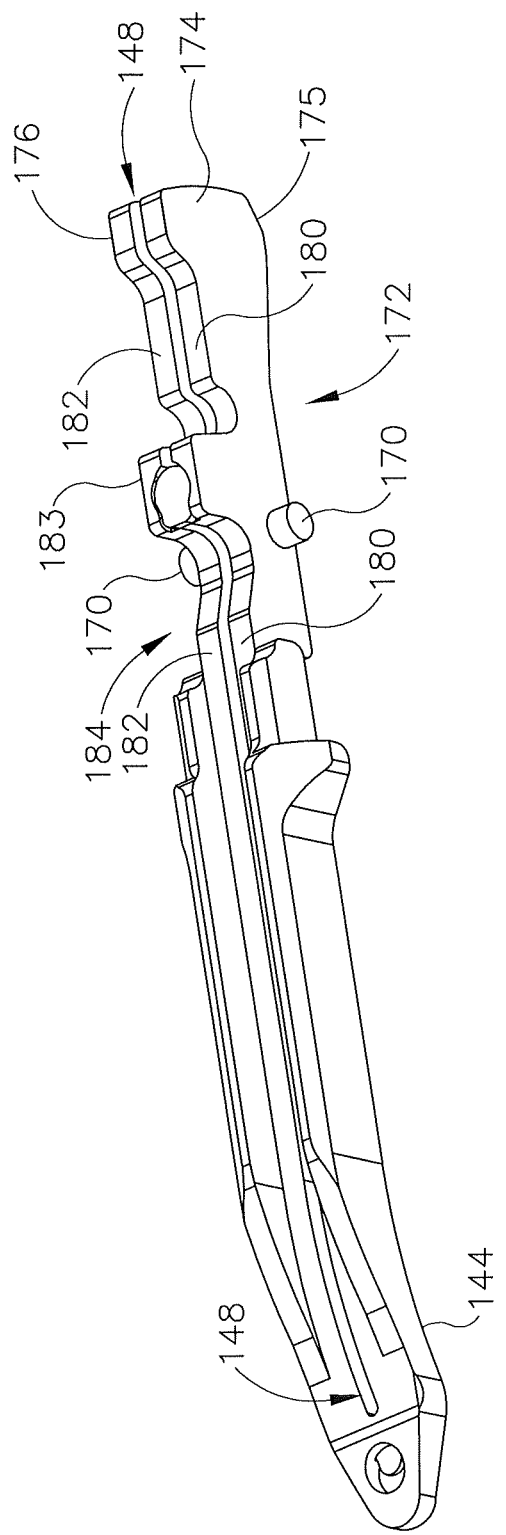
FIG. 7 depicts a perspective view of the upper jaw of the end effector of FIG. 6.

FIG. 7 shows pivot pins (170) disposed near and laterally extending from a proximal end of upper jaw (144). Upper jaw (144) includes lever arm (172) that extends proximally relative to pivot pins (170) and includes first lever arm segment (174) and parallel second lever arm segment (176). Slot (148) is defined between segments (174, 176). Slot (148) extends longitudinally toward a distal end of upper jaw (144) and is similar to slot (48) of upper jaw (44) described above. Slot (148) is sized and shaped to receive firing beam (160). Upper surfaces (180, 182) of segments (174, 176) extend toward a distal end of upper jaw (144). Upper surfaces (180, 182) together define a ramped and curved surface section (184) located above and distal to pivot pins (170). Referring to FIG. 5, segments (174, 176) of lever arm (172) are sized and shaped for pivotal receipt through lateral aperture (133) of outer sheath (132) of shaft (130). Lower jaw (142) includes slot (146) that extends toward a distal end of lower jaw (142) and is similar to slot (46) of lower jaw (42) described above. In particular, slots (146, 148) are vertically aligned and are configured to slidingly receive firing beam (160) as described in greater detail below.

Figure 8:
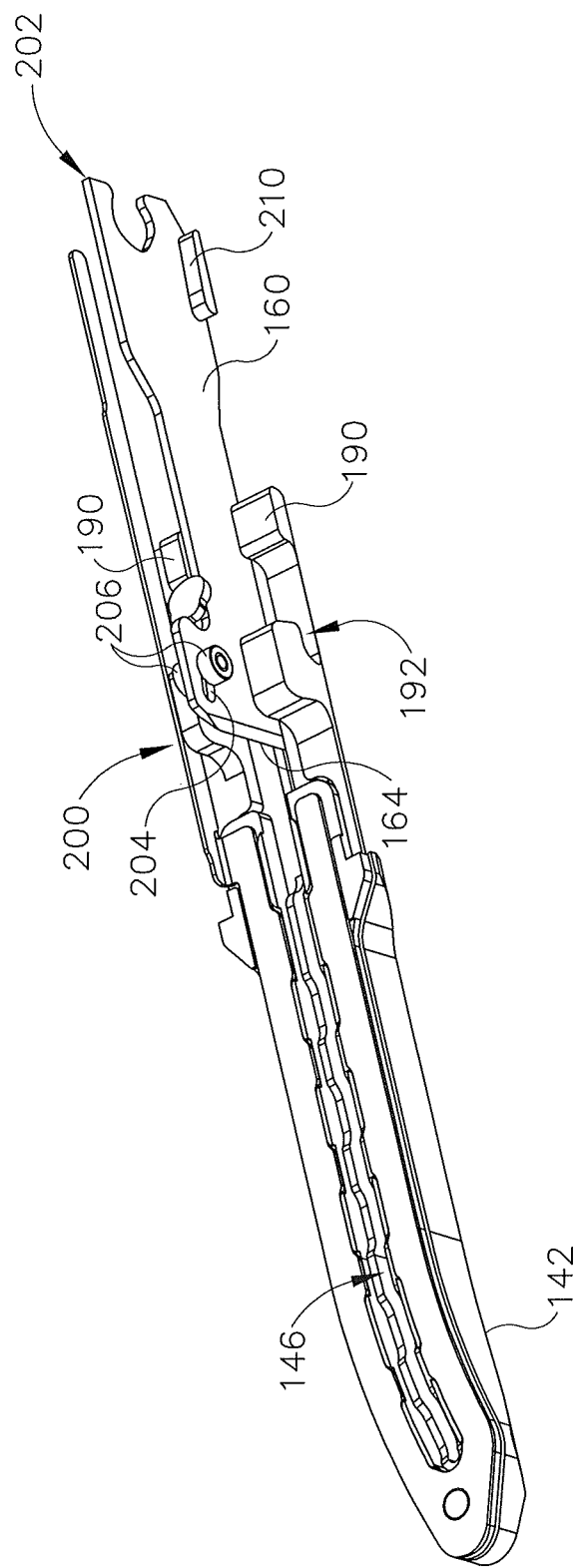
FIG. 8 depicts a perspective view of the lower jaw and attached firing beam of the end effector of FIG. 6.
Figure 10A:
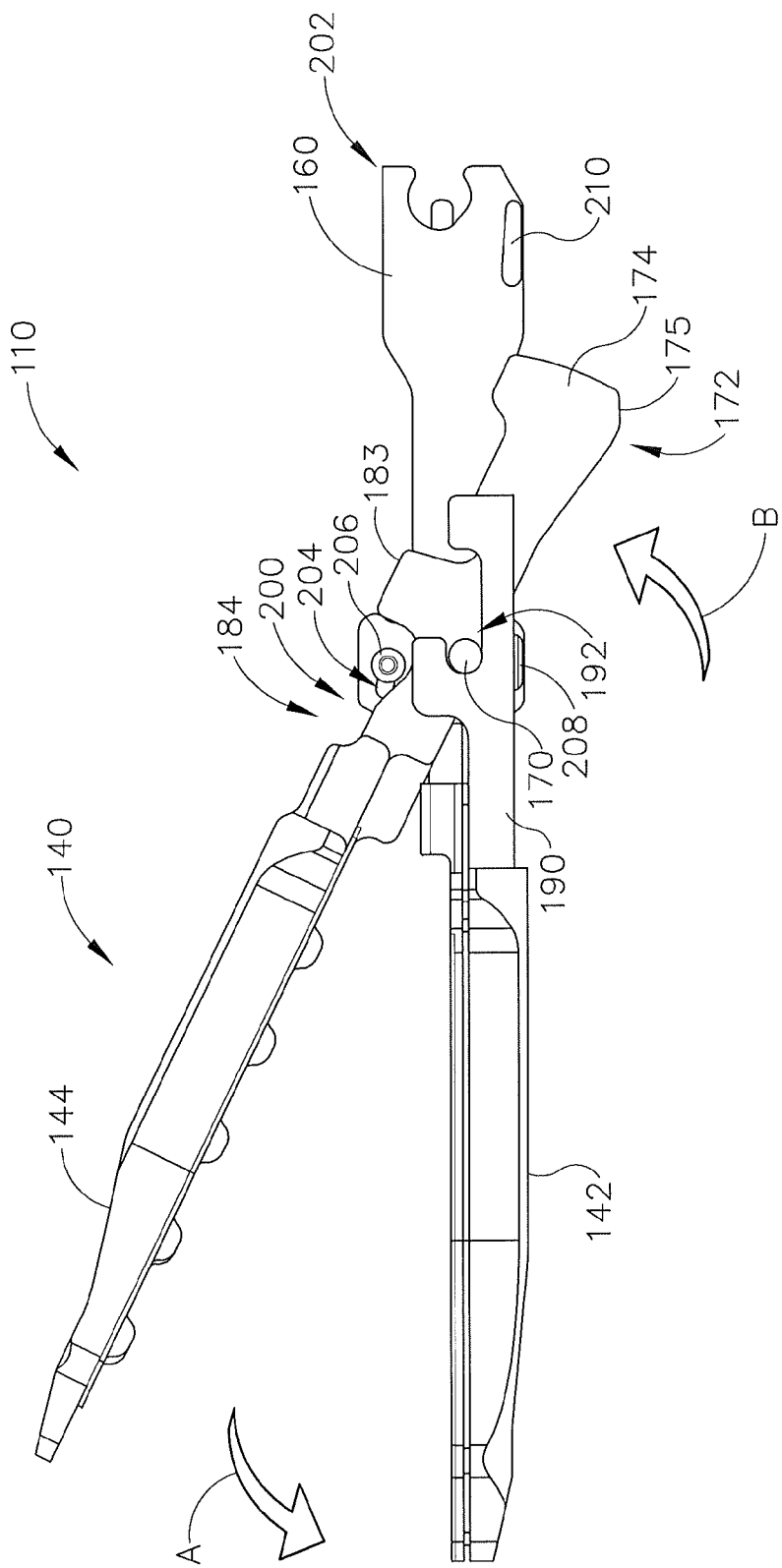
FIG. 10A depicts an elevation view of the end effector of FIG. 6, with the jaws in an open position and with the firing beam in a proximal position.

FIGS. 8 and 10A show lower jaw (142) and firing beam (160). A proximal end of lower jaw (142) includes pivot pin receiving arms (190), which each define pivot pin receiving groove (192). Groove (192) receives pivot pins (170), providing a pivoting coupling between jaws (142, 144).

Firing beam (160) includes distal end (200) and proximal end (202). Slot (204) is defined at distal end (200) and closure pin (206) extends laterally from each side of slot (204). Laterally extending ends of closure pin (206) have a width that is greater than a width of slot (204), and an intermediate section of closure pin (206) includes a width that is sized and shaped for sliding and rotatable receipt within slot (204). Thus, closure pin (206) is configured to rotate within slot (204) and translate within slot (204). In some versions, pin (206), slot (204), and/or other features of instrument (110) are constructed in accordance with at least some of the teachings of U.S. Pub. No. 2012/0083783, entitled "Surgical Instrument with Jaw Member," published Apr. 5, 2012, now U.S. Pat. No. 8,888,809, issued Nov. 18, 2015, the disclosure of which is incorporated by reference herein. A pair of distal closure flanges (208) (FIG. 6) extends laterally from firing beam (160) and is disposed below closure pin (206) and at a bottom distal end of firing beam (160). A pair of proximal flanges (210) is disposed at proximal end (202) of firing beam (160) and extends laterally from firing beam (160). The distal end of firing beam (160) presents cutting edge (164) for severing tissue captured between jaws (142, 144). In some instances, at least part of firing beam (160) is constructed in accordance with at least some of the teachings of U.S. patent application Ser. No. 13/692,202, entitled "Surgical Instrument with Curved Blade Firing Path," filed Dec. 3, 2012, now U.S. Pat. No. 9,078,677, issued Jul. 14, 2015, the disclosure of which is incorporated by reference herein. Other suitable configurations will be apparent to those of ordinary skill in the art in view of the teachings herein.

Figure 9:
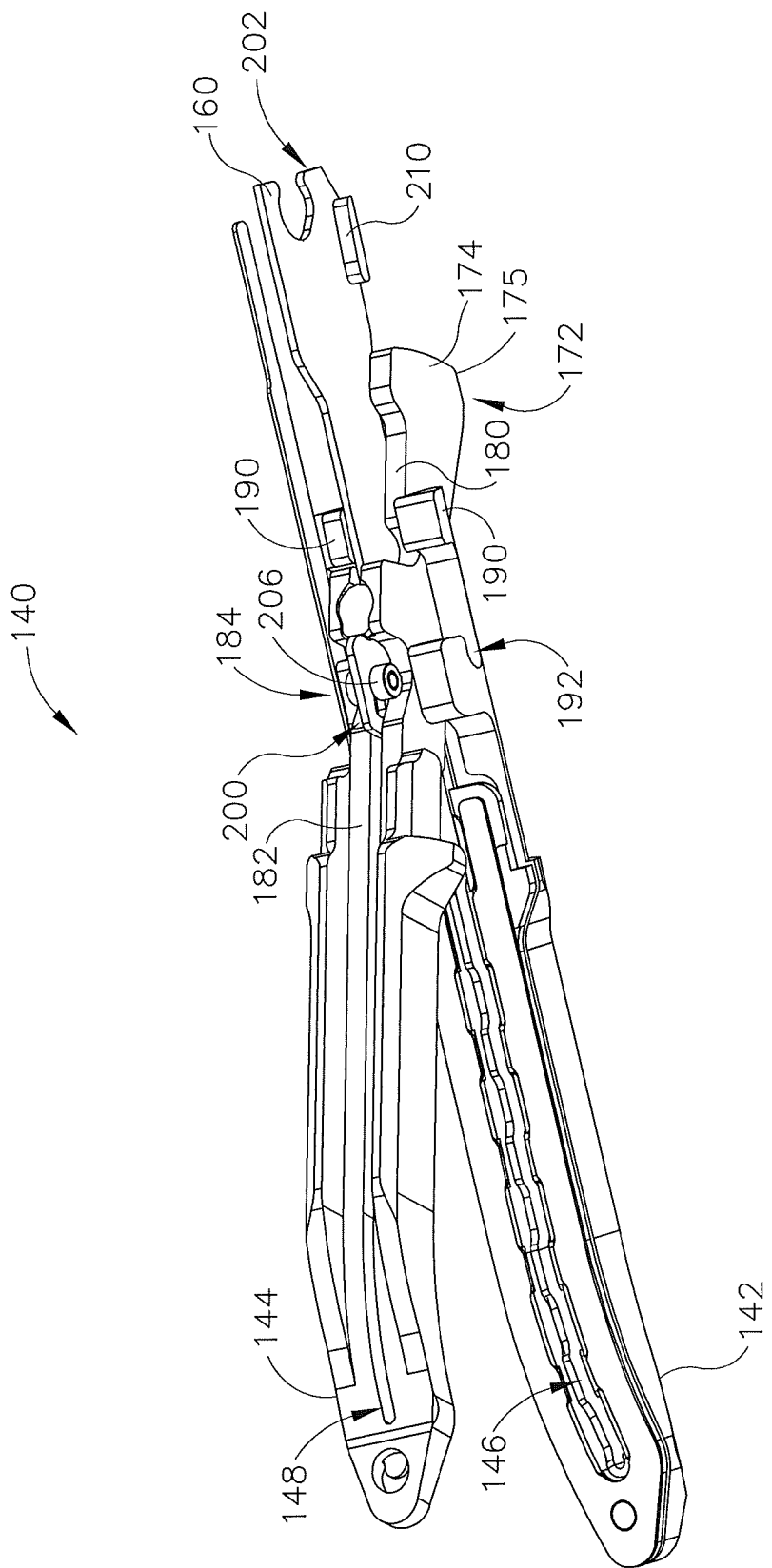
FIG. 9 depicts a perspective view of the upper and lower jaws and firing beam of the end effector of FIG. 6 assembled together.
Figure 10B:
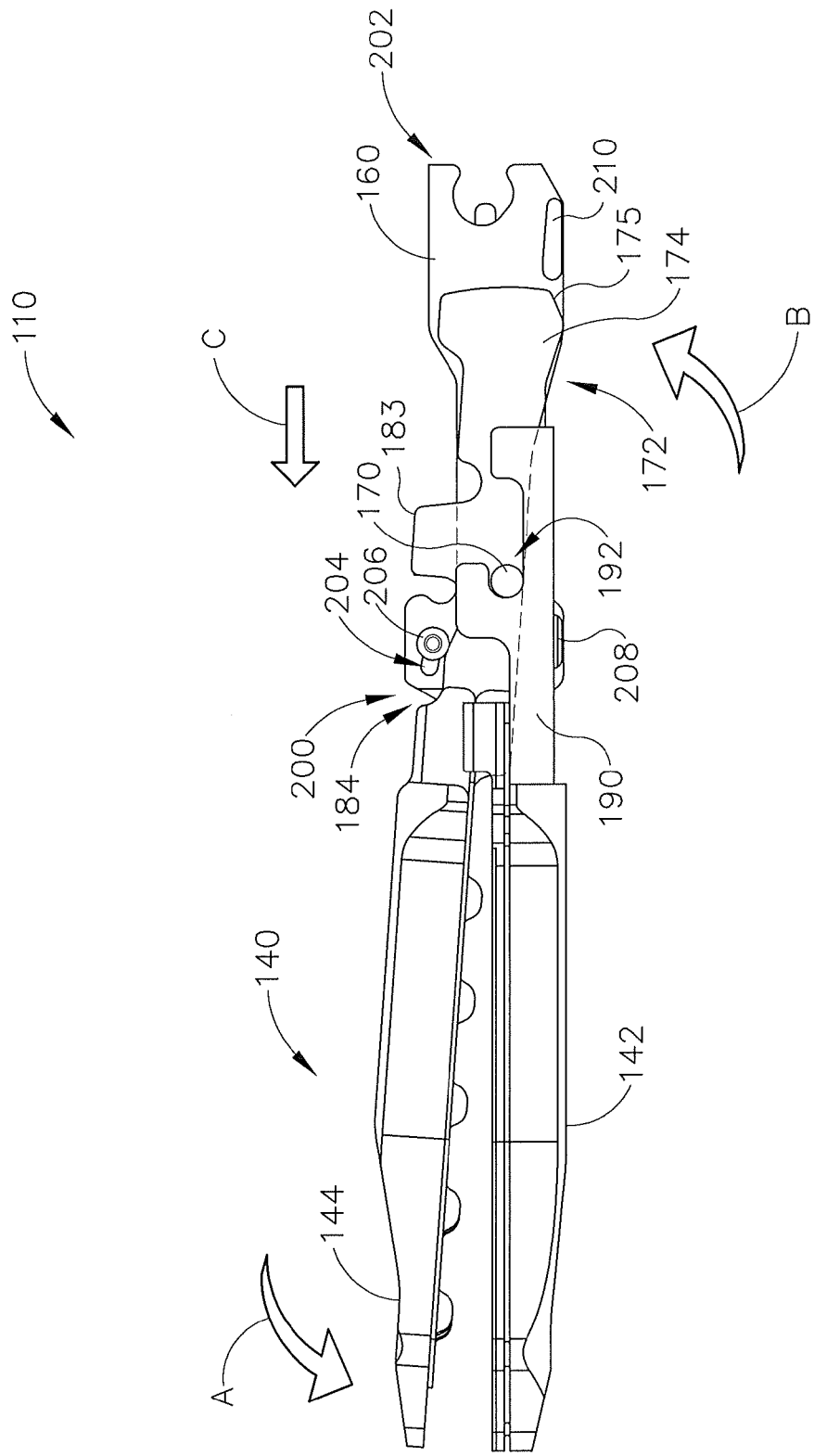
FIG. 10B depicts an elevation view of the end effector of FIG. 6, with the jaws in a partially closed position, and with the firing beam in a first distal position in which a proximal portion of the lever arm is adjacent to the pair of proximal flanges of the firing beam.
Figure 10C:
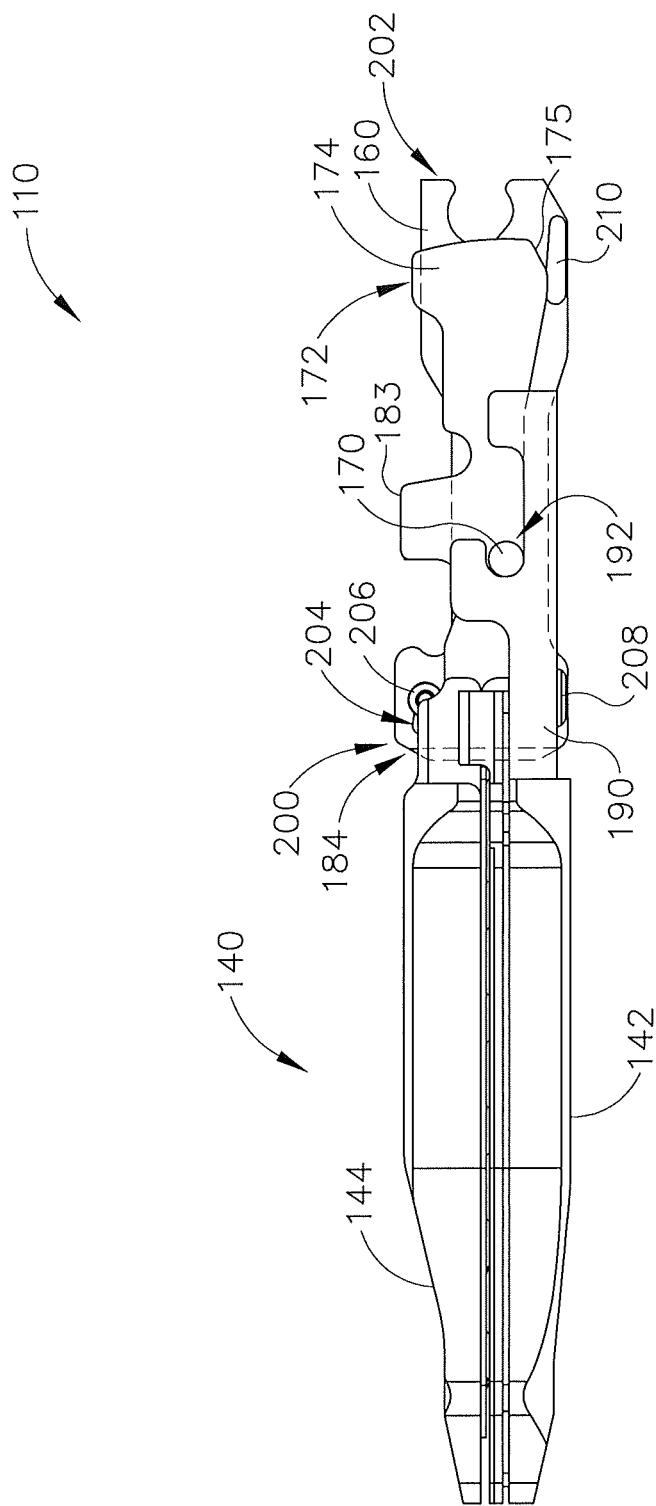
FIG. 10C depicts an elevation view of the end effector of FIG. 6, with the jaws in a fully closed position, and with the firing beam in a second distal position in which a proximal portion of the lever arm abuts a top portion of the pair of proximal flanges of the firing beam.
Figure 10D:
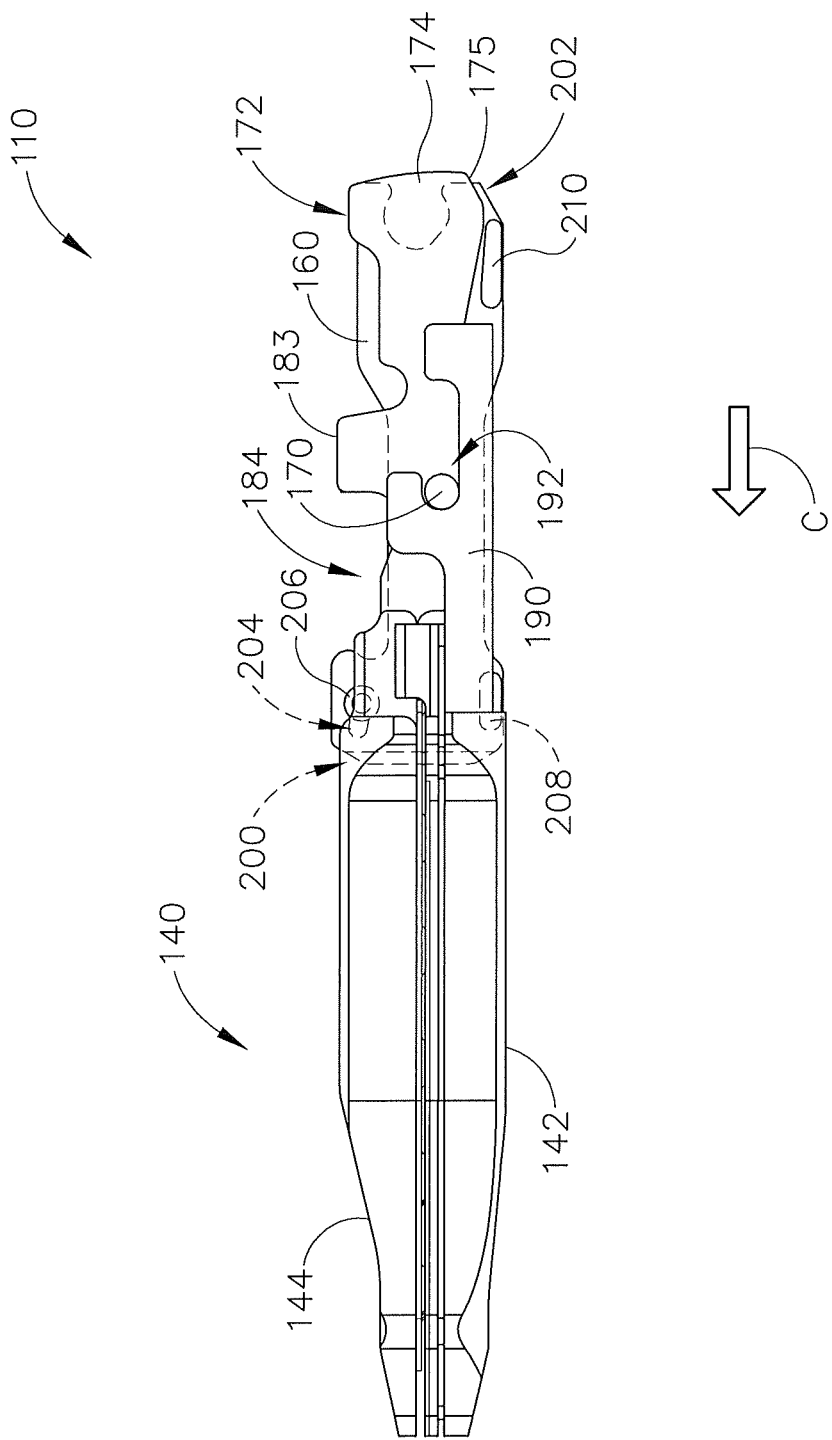
FIG. 10D depicts an elevation view of the end effector of FIG. 6, with the jaws in the fully closed position, and with the firing beam in a third distal position in which the pair of proximal flanges of the firing beam has cleared the proximal portion of the lever arm.
Figure 10E:
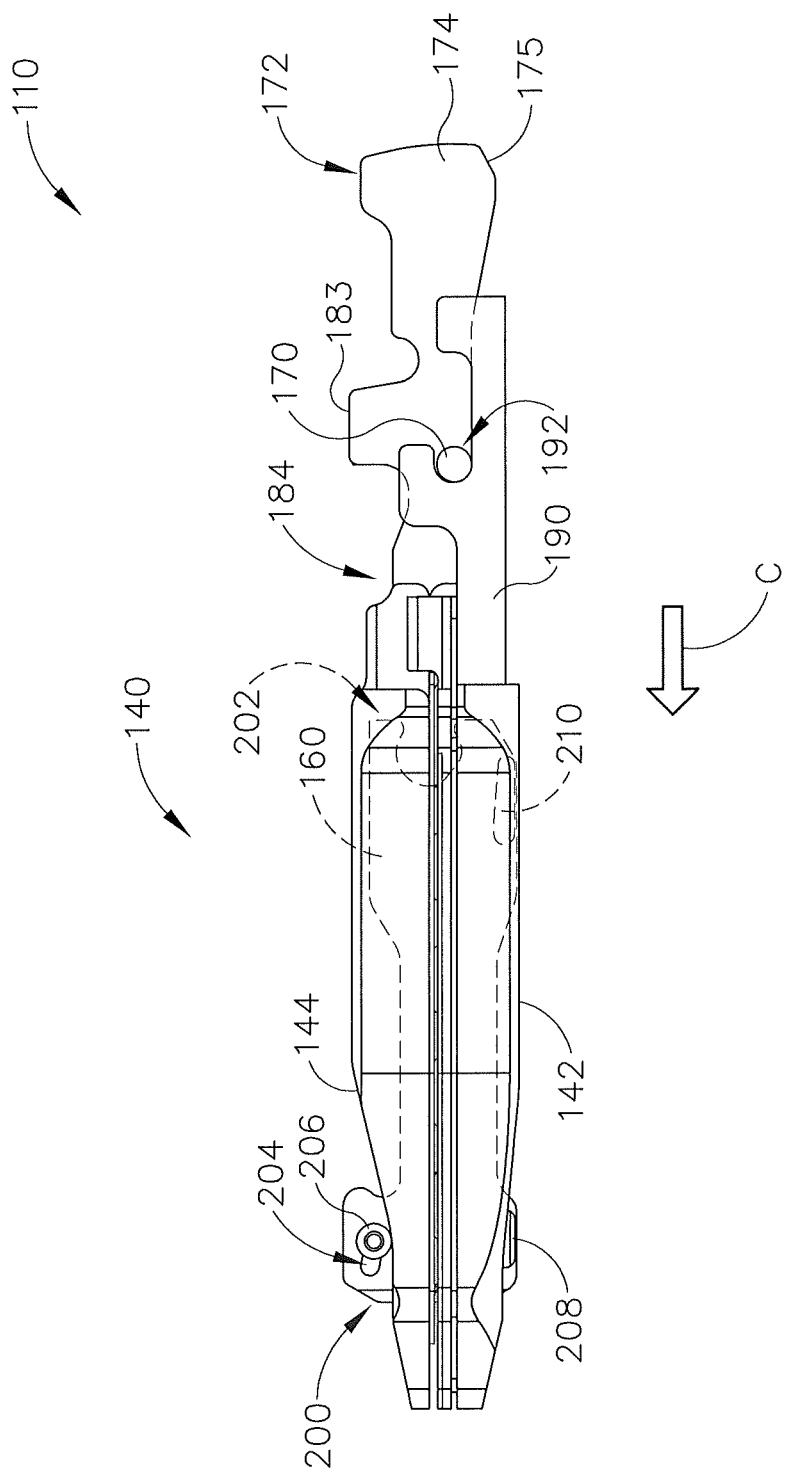
FIG. 10E depicts an elevation view of the end effector of FIG. 6, with the jaws in the fully closed position, and with the firing beam in a fourth, distal-most position.
Figure 10F:
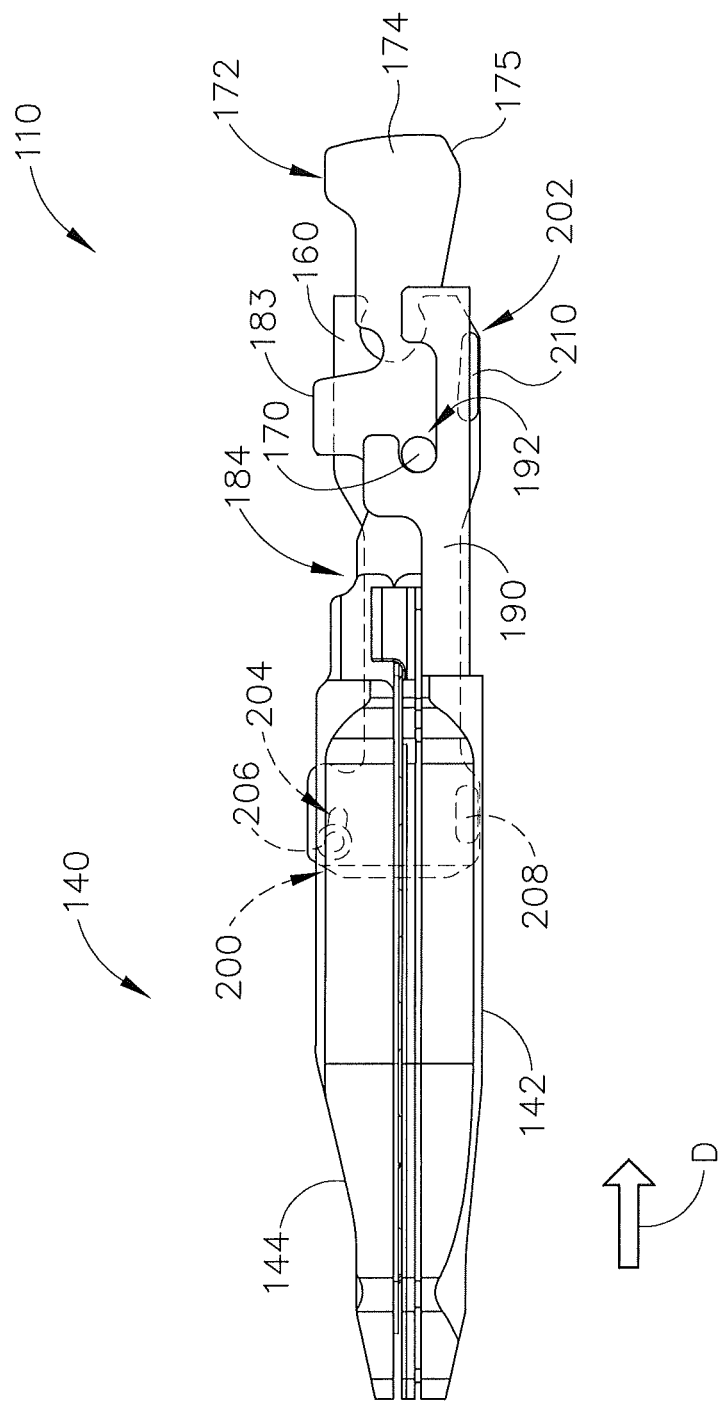
FIG. 10F depicts an elevation view of the end effector of FIG. 6, with the firing beam partially retracted from the distal-most position, in which the closure pin has slid to a distal slot position.

FIGS. 9-10F show assembled configurations of upper jaw (144), lower jaw (142), and firing beam (160). Pivot pins (170) of upper jaw (144) are received in pivot pin receiving groove (192) of lower jaw (142). As described in greater detail below, different features of firing beam (160) interact with upper jaw (144) at different stages of advancement of firing beam (160). These staged interactions may substantially reduce the force needed to advance firing beam (160).

FIG. 10A shows end effector (140) in an open position in which upper jaw (144) is pivoted away from lower jaw (142). A portion of lever arm (172) extends through aperture (133) of shaft (130). At this stage, closure pin (206) of firing beam (160) is received in curved surface section (184) of upper jaw (144). Firing beam (160) is operable to advance along slots (146, 148) of respective jaws (142, 144), while closure pin (206) and flanges (208) advance along exterior surfaces of slots (146, 148) to close jaws (142, 144) to a position shown in FIG. 10B. As seen in the transition from FIG. 10A to FIG. 10B, advancement of firing beam (160) drives closure pin (206) distally along curved surface section (184) of surfaces (180, 182) of upper jaw (144). Flanges (208) of firing beam (160) advance along exterior lower surfaces of lower jaw (142) adjacent to slot (146). This causes upper jaw (144) to begin closing with respect to lower jaw (142). In particular, a distal portion of upper jaw (144) pivots about pivot pins (170) in the direction of arrow (A) toward lower jaw (142); while lever arm (172) pivots about pivot pins (170) in the direction of arrow (B).

FIG. 10B shows end effector (140) in a partially closed position in which upper jaw (144) is slightly angled with respect to lower jaw (142). A proximal end of segment (174) of lever arm (172) has pivoted in the direction of arrow (B). It should be understood that closure pin (206) has provided the driving engagement with upper jaw (144) to pivot upper jaw (144) from the position shown in FIG. 10A to the position shown in FIG. 10B.

In some instances, proximal faces of segments (174, 176) are able to block proximal flanges (210) of firing beam (160) in the position shown in FIG. 10B. For example, if too much tissue is clamped between jaws (142, 144), proximal flanges (210) of firing beam (160) will run into proximal faces of segments (174, 176) of lever arm (172), which will prevent firing beam (160) from advancing in the direction of arrow (C). In such a position, lever arm (172) acts a stop to prevent the advancement of firing beam (160) to prevent closure of jaws (142, 144) on too much tissue, which prevents damage to the tissue clamped between jaws (142, 144) that may otherwise be severed by firing beam (160) without properly being sealed by jaws (142, 144). In addition or in the alternative, this may prevent damage to proximal flanges (210) and/or closure pin (206) that might otherwise be caused by continued distal advancement of firing beam (160). If the thickness of tissue between jaws (142, 144) is appropriate, firing beam (160) may continue advancing and lever arm (172) will continue pivoting in the direction of arrow (B) to a position shown in FIG. 10C. An appropriate thickness of tissue may be found in, for example, a vessel having a width of about 7 mm or less.

FIG. 10C shows end effector (140) in a closed position in which upper jaw (144) is substantially parallel to lower jaw (142). In this closed position, lever arm (172) is disposed in shaft (130) in a clamping position and camming faces (175) of segments (174, 176) cam against top portions of proximal flanges (210). When first in the clamping position shown in FIG. 10C, flanges (210) are advanced against lever arm (172) to provide a closure force between jaws (142, 144), and force applied by flanges (210) against lever arm (172) assists to provide additional mechanical advantage to the closure of jaws (142, 144). Thus, at this stage, flanges (210) are providing the driving engagement with upper jaw (144) to continue pivoting upper jaw (144), thereby further clamping tissue between jaws (142, 144).

A proximal end of lever arm (172) may be disposed about 3 to 4 times a greater distance away from pivot pins (170) than slot (204) of firing beam (160) is spaced away from pivot pins (170). In the clamping position, lever arm (172) transfers force over this extra distance to close jaws (142, 144) while providing an improved mechanical advantage and resolution (indicating a reduced tolerance sensitivity) over use of closure pin (206) alone. Lever arm (172) may be comprised of a bowing and flexible material to allow for an interference fit between lever arm (172) and flanges (210) to lessen a tolerance stack between lever arm (172) and flanges (210). Other suitable materials for lever arm (172) are possible as will be apparent to those of ordinary skill in the art in view of the teachings herein.

When in the clamping position shown in FIG. 10C, with jaws (142, 144) closed against one another, jaws (142, 144) may utilize electrodes similar to those described above for jaws (42, 44) to seal portions of the clamped tissue between jaws (142, 144) before or without severing the tissue with firing beam (160). If the surgeon does not wish to sever tissue with firing beam (160), the surgeon may simply retract firing beam (160) at this stage. Closure pin (206) will eventually cam against ramped and curved surface section (184) to pivot upper jaw (144) back to an open, unclamped position. An active electrode may also be exposable to tissue at a distal end of jaws (42, 44) to use energy from the electrode to soften the tissue for blunt dissection, for example. Lower jaw (142) may have an overmolded electrode disposed along an exterior of lower jaw (142) rather than an underside of lower jaw (142). Some versions of instrument (110) may provide audible, visual, and/or tactile feedback to indicate to the surgeon that instrument (110) has reached the stage shown in FIG. 10C. Various suitable ways in which this may be carried out will be apparent to those of ordinary skill in the art in view of the teachings herein.

In instances where the surgeon wishes to continue advancing firing beam (160) distally from the position shown in FIG. 10C to sever tissue clamped between jaws (142, 144), firing beam (160) eventually reaches the position shown in FIG. 10D. At this stage, flanges (210) have disengaged lever arm (172). Closure pin (206) now drives against upper jaw (144) once again to maintain a clamping force against upper jaw (144), in cooperation with engagement between distal closure flanges (208) and lower jaw (142). It should be noted that firing beam (160) may begin to sever tissue clamped between jaws (142, 144) at this stage. It should also be noted that closure pin (206) is disposed at a proximal end of slot (204) as firing beam (160) advances in the direction of arrow (C). Furthermore, closure pin (206) rotates within slot (204) during advancement of firing beam (206), which acts to reduce the force to fire firing beam (160). In particular, closure pin (206) rotates about a longitudinal axis defined by closure pin (206). In addition or in the alternative, the outer portions of closure pin (206) may be fitted with rotatable bushings, rollers, or other features that reduce friction between closure pin (206) and upper jaw (144).

FIG. 10E shows a fired position in which with firing beam (160) has advanced in the direction of arrow (C) to a distal-most position at the distal ends of jaws (142, 144). At this stage, firing beam (160) has completely severed tissue clamped between jaws (142, 144). To the extent that electrodes of jaws (142, 144) have not already been activated to seal tissue at each side of firing beam (160), such electrodes may be activated at this stage.

FIG. 10F shows a retraction of firing beam (160) away from the fired position. When firing beam (160) is retracted in the direction of arrow (D) back to the proximal position, closure pin (206) slides to the distal end of slot (204). Slot (204) has a curved profile such that closure pin (206) is slightly more vertically displaced from the upper surface of upper jaw (144) when closure pin (206) is in the distal end of slot (204). This additional vertical displacement reduces the bearing force of closure pin (206) against upper jaw (144), thereby reducing friction between closure pin (206) and upper jaw (144). In addition, closure pin (206) rotates within slot (204) as noted above, to further reduce friction against upper jaw (144). These features thus both ultimately reduce the force required to return firing beam (160) from the distal position shown in FIG. 10E to the proximal position shown in FIG. 10A.

In some versions, lever arm (172) is resilient, such that lever arm (172) may bend while applying a force at the distal tip of upper jaw (144) as firing beam (160) is advanced distally. By way of example only, lever arm (172) may provide an interference fit with flanges (210) of firing beam (160) such that when jaws (142, 144) are fully closed and firing beam (160) is at a distal-most position, flanges (210) bear upwardly into drive lever arm (172), which in turn provides a downward force at the distal tip of upper jaw (144). It should be understood that making lever arm (172) resilient may generally limit the load on jaws (142, 144). Making lever arm (172) resilient may also limit the pressure on tissue that is clamped between jaws (142, 144). Furthermore, a resilient lever arm (172) may reduce tolerance sensitivities of firing beam (160).

It should also be understood that lower jaw (142) may include a lower cam surface that is engaged by flanges (210) of firing beam (160) while flanges (210) engage lever arm (172). Flanges (210) may thus effectively engage both jaws (142, 144) simultaneously while driving jaw (144) to the closed position. By way of example only, this lower cam surface of lower jaw (142) may engage the bottom surfaces of flanges (210) while lever arm (172) engages the top surfaces of flanges (210). It should be understood that in some such versions, the force required to close jaws (142, 144) during such engagement is borne solely by flanges (210) and firing beam (160).

While the above described features are described for radio frequency based surgical instrument (110), similar features could be used for various other kinds of instruments such as an ultrasonic surgical instrument or linear stapler (e.g., endocutter) instruments, including but not limited to variations of such instruments described in various references cited herein.

B. Exemplary Upper Jaw with a Pair of Lever Arms

FIG. 11 shows an exemplary end effector (340) of instrument (310) that is similar to end effector (140) described above except that end effector (340) includes a pair of lever arms (372, 373). End effector (340) includes upper jaw (344), lower jaw (142), and firing beam (160). Lever arm (373) is attached to and pivotable about a proximal end of lever arm (372) at one end and is slidably disposed in shaft (330) via a pin and slot connection, for example. Other suitable connections will be apparent to those of ordinary skill in the arm in view of the teachings herein.

When upper jaw (344) is rotated about pivot pins (370) in the direction of arrow (A), lever arm (372) is rotated in the direction of arrow (B) and lever arms (372, 373) are received within an aperture defined in the underside of outer sheath (332) of shaft (330). As lever arm (372) is rotated in the direction of arrow (B), first lever arm (373) moves to a position clearing and above flanges (210) of firing beam (160) while lever arm (372) moves to a similar position. In these positions, lever arms (372, 373) are substantially parallel to one another and substantially aligned with a longitudinal axis of outer sheath (332).

Lever arms (372, 373) include gaps or slots between lever arm segments that are sized and shaped to slidingly receive firing beam (160). When lever arms (372, 373) are disposed above flanges (210), end effector (340) and instrument (310) operate in a manner similar to that described above for end effector (140) and instrument (110). The presence of lever arm (373) may prevent the proximal end of lever arm (372) from getting snagged on tissue when jaws (142, 344) are in an open configuration.

While the above described features are described for radio frequency based surgical instrument (310), similar features could be used for various other kinds of instruments such as an ultrasonic surgical instrument or linear stapler (e.g., endocutter) instruments, including but not limited to variations of such instruments described in various references cited herein.

III. Miscellaneous

It should be understood that any of the versions of electrosurgical instrument (10) described herein may include various other features in addition to or in lieu of those described above. By way of example only, any of the devices herein may also include one or more of the various features disclosed in any of the various references that are incorporated by reference herein.

It should also be understood that any of the devices described herein may be modified to include a motor or other electrically powered device to drive an otherwise manually moved component. Various examples of such modifications are described in U.S. Pub. No. 2012/0116379, entitled "Motor Driven Electrosurgical Device with Mechanical and Electrical Feedback," published May 10, 2012, now U.S. Pat. No. 9,161,803, issued Oct. 20, 2015, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An apparatus for operating on tissue, the apparatus comprising:
   (a) an end effector assembly comprising:
      (i) an upper jaw having a proximal portion and a distal portion, wherein the proximal portion of the upper jaw defines a lever arm,
      (ii) a lower jaw pivotally connected to the upper jaw at a pivot point, wherein the distal portion of the upper jaw extends distally past the pivot point wherein the lever arm extends proximally relative to the pivot point from the pivot point along the proximal portion of the upper jaw, and (iii) a firing beam configured to be received within slots defined in the upper and lower jaws to close the jaws, wherein the firing beam has a proximal jaw driving feature configured to engage a portion of the lever arm extending proximally relative to the pivot point from the pivot point along the proximal portion of the upper jaw, wherein the proximal driving feature is configured to impart force to the lever arm about the pivot point and thereby drive the upper jaw closed toward the lower jaw;

(b) a body operable to communicate with the end effector assembly; and (c) a shaft extending between the end effector assembly and the body, wherein the shaft comprises an outer sheath, wherein the outer sheath defines an aperture, and wherein a portion of the lever arm that extends from the pivot point along the proximal portion of the upper jaw extends through the aperture in at least one pivotal position of the upper jaw.

2. The apparatus of claim 1, wherein the upper and lower jaws comprise electrodes configured to seal tissue.

3. The apparatus of claim 1, further comprising a link disposed between the lever arm and the outer sheath.

4. The apparatus of claim 1, wherein the firing beam comprises a proximal pair of laterally extending flanges and a distal closure pin, wherein the flanges and the pin are configured to cooperate with the upper jaw.

5. The apparatus of claim 4, wherein the firing beam further comprises a slot, wherein the ends of the closure pin extend laterally from the slot of the firing beam, wherein the closure pin is slidable within the slot of the firing beam.

6. The apparatus of claim 4, wherein at least part of the closure pin is rotatable relative to the firing beam.

7. The apparatus of claim 4, wherein an upper surface of the upper jaw defines one of the slots, wherein the closure pin is configured to advance across the upper surface of the upper jaw, wherein a lower surface of the lower jaw defines the slot of the lower jaw, wherein the proximal pair of laterally extending flanges are configured to advance across the lower surface of the lower jaw.

8. The apparatus of claim 4, wherein the lever arm is configured to rotate about the pivot point from a first position in which the upper jaw is open with respect to the lower jaw to a second position in which the jaws are closed.

9. The apparatus of claim 8, wherein the lever arm comprises a camming surface, wherein the closure pin is operable to drive the upper jaw to a camming position in which the proximal pair of laterally extending flanges engage the camming surface of the lever arm.

10. The apparatus of claim 9, wherein the proximal pair of laterally extending flanges of the firing beam are configured to distally advance below the lever arm to a clearance position in which the proximal pair of laterally extending flanges of the firing beam are clear from the lever arm such that interaction of the closure pin with the upper jaw is configured to control the closure of the jaws.

11. The apparatus of claim 9, wherein the upper and lower jaws comprise electrodes configured to seal tissue, and wherein the jaws in a closed configuration are configured to seal tissue prior to the firing beam reaching a tissue cutting position.

12. The apparatus of claim 9, wherein the lever arm is configured to rotate to a third position between the first position and the second position, wherein the lever arm is configured to act as a stop against the proximal pair of laterally extending flanges in response to being in the third position to prevent the firing beam from being able to advance.

13. The apparatus of claim 4, wherein the firing beam further comprises a distal pair of laterally extending flanges, wherein the distal pair of laterally extending flanges is substantially vertically aligned with the distal closure pin.

14. The apparatus of claim 4, wherein the distal closure pin is configured to drive the upper jaw to an open position in response to proximal retraction of the firing beam to a proximal position, wherein the proximal pair of laterally extending flanges are configured to be located proximal to the lever arm in response to the firing beam being moved to the proximal position.

15. The apparatus of claim 1, wherein the firing beam further comprises a slot, wherein the closure pin is located in a proximal position in the slot of the firing beam in response to a distal advancement of the firing beam.

16. The apparatus of claim 15, wherein the closure pin is slidable within the slot and is located in a distal position in the slot in response to a proximal retraction of the firing beam.

17. The apparatus of claim 1, wherein the lever arm comprises a pair of segments defining a portion of the slot of the upper jaw, wherein the pair of segments are configured for receipt through the aperture defined in the outer sheath.

18. An apparatus for operating on tissue, the apparatus comprising:

(a) an end effector assembly comprising:

(i) an upper jaw having a proximal portion, wherein the proximal portion of the upper jaw defines a lever arm and a slot, (ii) a lower jaw pivotally connected to the upper jaw at a pivot point, wherein the lower jaw defines a slot, wherein the lever arm extends proximally relative to the pivot point from the pivot point along the proximal portion of the upper jaw, and (iii) a firing beam configured to be received within the slots defined in the upper and lower jaws to close the jaws, wherein the firing beam comprises a distal jaw driving feature and a proximal jaw driving feature, wherein the driving features are configured to drive the upper jaw closed in different stages, each stage being based on the longitudinal position of the firing beam relative to the upper jaw and the lower jaw, wherein the proximal driving feature is configured to engage a portion of the lever arm extending proximally relative to the pivot point from the pivot point along the proximal portion of the upper jaw in at least one of the different stages, wherein the proximal driving feature is configured to impart force to the lever arm about the pivot point and thereby drive the upper jaw closed toward the lower jaw;

(b) a body operable to communicate with the end effector assembly; and (c) a shaft extending between the end effector assembly and the body.

19. The apparatus of claim 18, wherein the distal jaw driving feature comprises a closure pin and a distal pair of laterally extending flanges, wherein the proximal jaw driving feature comprises a proximal pair of laterally extending flanges, wherein the distal jaw driving feature is operable to cam against surfaces defining slots in the upper and lower jaws such that the closure pin cams against an upper jaw surface and the distal pair of laterally extending flanges cam against a lower jaw surface, and wherein the proximal jaw driving feature is operable to cam against the lever arm.

20. An apparatus for operating on tissue, the apparatus comprising:
(a) an end effector assembly comprising:
  (i) an upper jaw having a proximal portion, wherein the proximal portion of the upper jaw defines a lever arm having a camming surface and a proximal surface,
  (ii) a lower jaw pivotally connected to the upper jaw at a pivot point, wherein the lever arm extends proximally relative to the pivot point from the pivot point along the proximal portion of the upper jaw, and
  (iii) a firing beam configured to be received within slots defined in the upper and lower jaws to close the jaws, wherein the firing beam comprises a distal jaw driving feature and a proximal jaw driving feature, wherein the driving features are configured to drive the upper jaw closed in different stages, each stage being based on the longitudinal position of the firing beam relative to the upper jaw and the lower jaw, wherein the proximal surface of the lever arm is operable to abut the proximal jaw driving feature of the firing beam in a first stage, wherein the camming surface of the lever arm is operable to cam against the proximal jaw driving feature in a second stage such that the proximal jaw driving feature imparts force to the lever arm about the pivot point and thereby drives the upper jaw closed toward the lower jaw, and wherein the proximal jaw driving feature is operable to clear the lever arm in a third stage;
(b) a body operable to communicate with the end effector assembly; and
(c) a shaft extending between the end effector assembly and the body.

* * * * *